United States Patent [19]

Sherman

[11] 4,401,582

[45] * Aug. 30, 1983

[54] SOFT CONTACT LENS AMBIENT TEMPERATURE DISINFECTANT SOLUTION AND METHOD

[75] Inventor: Guy J. Sherman, Mandeville, La.

[73] Assignee: Sherman Laboratories, Inc., Abita Springs, La.

[*] Notice: The portion of the term of this patent subsequent to Oct. 26, 1999 has been disclaimed.

[21] Appl. No.: 331,150

[22] Filed: Dec. 16, 1981

Related U.S. Application Data

[63] Continuation-in-part of Ser. No. 228,562, Jan. 26, 1981, Pat. No. 4,367,157, which is a continuation-in-part of Ser. No. 37,645, May 10, 1979, Pat. No. 4,356,100.

[51] Int. Cl.$^3$ ............................................. C11D 3/48
[52] U.S. Cl. ...................................... 252/90; 134/42; 252/89.1; 252/106; 252/173; 252/DIG. 14; 424/280
[58] Field of Search .......... 252/106, DIG. 14, 174.24, 252/89.1, 173, 90; 424/78, 80, 146, 280; 134/40, 134/42

[56] References Cited

U.S. PATENT DOCUMENTS 3,329,607  7/1967  Colobert ........................ 252/181 X
4,126,587  11/1978  Sibley et al. ..................... 134/40 X
4,199,469  4/1980  Walzer ............................. 134/41 X

FOREIGN PATENT DOCUMENTS 52-18708  2/1977  Japan .
2003033   3/1979  United Kingdom .

*Primary Examiner*—P. E. Willis, Jr.
*Attorney, Agent, or Firm*—Winburn & Gray, Ltd.

[57] ABSTRACT

Aqueous compositions for the ambient temperature or cold disinfection of soft contact lenses during non-wearing periods is provided. The composition includes water and a disinfectant composition comprising an effective amount of an ascorbic acid compound for killing bacteria, generally between about 0.1% and 20% by weight of the total aqueous composition, calculated as ascorbic acid. The disinfectant composition may also include a potentiating agent to further enhance the kill factor of ascorbic acid with respect to fungi, yeasts and viruses. A method is provided for treating the lenses to kill bacteria associated with the lenses.

16 Claims, No Drawings

SOFT CONTACT LENS AMBIENT TEMPERATURE DISINFECTANT SOLUTION AND METHOD

RELATED APPLICATIONS

This application is a continuation-in-part application of application Ser. No. 228,562 filed Jan. 26, 1981, now U.S. Pat. No. 4,437,157, which is a continuation-in-part application of Ser. No. 37,645 filed May 10, 1979 now U.S. Pat. No. 4,356,100.

BACKGROUND OF THE INVENTION

Just as there are marked differences in the structure and composition of hard and soft contact lenses, there are also marked differences in the maintenance and care or treatment of the various types of hard, semi-hard and soft lenses. While patient care and treatment of hard contact or conventional contact lenses is relatively simple and uncomplicated, the proper care and treatment of the newer soft and hydrophilic lenses has proved to be more complex and time consuming.

The primary difference between the conventional hard contact lens and the more complex soft lenses is the marked increase in the polar or water attracting centers of the hydrophilic gel material. It is this property of the hydrophilic gel lens that gives the soft lens its own unique physical properties and clinical behavior. This polar or water attracting center of the gel material is represented in the hydroxyethyl methacrylate bond as a hydroxyl group (-OH) which attracts and holds large amounts of water. It is this high water content held in the expanded matrix of the hydrophilic gel lens which leads to the special difficulties in and disinfecting or asepticising the soft hydrophilic lens. The hydrophilic nature of soft contact lenses makes the lenses vulnerable to bacterial contamination. While studies have demonstrated that bacteria cannot penetrate the actual intramolecular pores of the hydrophilic lens, except in defective lenses, the bacteria have an affinity for the protein and tear deposits on the surfaces of the lens matrix. In particular, the tears and fluids absorbed by the soft lenses serve as excellent bacterial culture media. If defects or nicks occur in the lens either during manufacture or subsequent patient wear, bacteria may find a haven to grow and be sheltered from superficial lens cleaning and disinfection.

Potentially harmful fungi also prove a possible danger to the soft contact lens. Fungi, like bacteria, can thrive in tear secretions or deposits and penetrate the lens material directly if enzymatic degradation of the lens material has taken place.

Other problems can accrue from incorrect and careless handling of the soft lenses by the patient himself. Many potential contaminants and lens deposits can be transferred from unwashed fingers to the surface of the soft lens. These include oily deposits from the skin, sweat, skin lotions and creams, mascara, detergents, lipstick and even nicotine. Controlled studies have demonstrated that bacterial contaminants occur in 43% of the makeup used by women, and fungal contaminants in 12%. Attempts to effect sterilization of the lenses by boiling, for example, can be cumbersome in addition to causing permanent damage to the lenses if done improperly. If the patient has used impure water for storage and rinsing of the lenses, undesirable deposits such as calcium, iron and insoluble divalent and trivalent metallic salts as well as other chemical deposits can collect on the lens surfaces.

Therefore, a need has arisen for an effective composition to counteract and mitigate the above described effects of improper hygiene and lens handling as well as to provide optimum disinfection and storage of the soft lens between lens wearing periods. In addition, the active ingredients of an effective contact lens solution should preferably: (1) disinfect clean soft lenses within a period of four to six hours and produce D values of a 90% kill rate of microorganisms, selected fungal and yeast organisms, and viral agents such as herpes simplex; (2) not be easily inactivated by small amounts of proteins, lipids or other tear and extraneous components and deposits; (3) not bind to protein or other lens surface deposits from the eye; and (4) not react with or absorb to the soft lens material or matrix. For example, several antiseptic agents which meet the above requirement for rapid and effective kill of a broad range of microorganisms have proved to be unsuitable for use in soft lens treatment solutions, in that these agents are incompatible with the soft lens material or bind with protein deposits on the surfaces of the lens matrix. Other antiseptic agents are unacceptable for use in soft lens solutions since they are concentrated by the lens material, to the extent that they cause discomfort and potential damage to the corneal surface of the wearer's eyes. Benzalkonium chloride is one such antiseptic agent which meets the requirements for effective and rapid killing of microorganisms but is unacceptable because it binds with many types of soft lens material and also binds with protein deposits on the lens surface.

One type of cold disinfecting solution for soft contact lenses uses chlorohexidine. However, chlorohexidine is absorbed by the soft contact lens material and gradually eluded into the eye often causing excessive burning, irritation and red eye, which can prevent the patient from wearing the lenses.

Therefore, a need has arisen for a highly effective cold storage and disinfecting solution and method for the overnight or interim disinfection and storage of soft and semi-hard contact lenses which meet the aforesaid requirements.

SUMMARY OF THE INVENTION

In accordance with the present invention, an aqueous storage and disinfecting solution containing ascorbic acid for the ambient temperature or cold storage and disinfection of soft and semi-hard contact lenses is provided. More particularly, the invention provides an effective ambient temperature storage and disinfecting solution for the disinfection and storage of hydrophilic gel lenses, semi-hard contact lenses and gelflex material soft lenses including, for example, the following plastic gel materials: hydroxyethyl methacrylate (HEMA) or its analogues, ethlene glycol dimethacrylate (EGMA) or its analogues, polymethyl methacrylate (PMMA) or its analogues, the relatively new semi-hard contact lens material cellulose-acetate-butyrate (CAB) and silicone polymers.

In accordance with another aspect of the present invention, a method for treating a contact lens is provided to kill bacteria that may be associated with the lens which method comrises contacting the lens with an aqueous composition containing a disinfectant ascorbic acid compound present in an effective concentration for killing bacteria and for a time sufficient to kill bacterial. The method is especially suitable for treating soft contact lenses. No heating is required and therefore, problems associated with elevated temperature treatment are eliminated.

The aqueous composition in accordance with the invention contains a disinfectant ascorbic acid compound that is present in an effective amount or concentration for killing bacteria. Suitable disinfectant ascorbic acid compounds include, for example, ascorbic acid and salts of ascorbic acid. The ascorbic acid compound should not be deleterious to the contact lens material. More particularly, suitable ascorbic acid compounds include ascorbic acid, disinfectant salts of ascorbic acid such as sodium ascorbate, calcium ascorbate and mixtures thereof. Generally, an effective concentration of the ascorbic acid compound is between about 0.1% and 20.0% calculated as ascorbic acid, by weight of the total composition.

An effective amount of a potentiating agent compound for enhancing the effectiveness of the ascorbic acid compound is preferably included. Such compounds include, trimethoprim (also known as 2,4-Diamino-5-(3,4,5-trimethoxygenzyl)-pyrimidine, thimerosal (also known as sodium ethylmercurithiosalicylate) and mixtures thereof. The combination of the ascorbic acid compound with a potentiating agent compound provides an ambient temperature disinfecting solution that is effective in killing microorganisms, fungal organisms and viral agents such as herpes simplex. Generally, the potentiating agent compound is present in an amount of between about 0.0001% and 5.0% by weight of the total composition.

The remainder of the composition may comprise solely water or may include various alkaline metal and alkaline earth metal water soluble salts to provide an aqueous composition salt content equivalent to about 0.8% to about 1.8% sodium chloride by weight of the total aqueous composition. A humectant such as propylene glycol may be optionally included in the composition. Further, a salt of ethylenediaminetetraacetic acid may be included as a buffering agent.

To provide a more stable composition, monothioglycerol may be included in the compositions of the present invention in an effective amount for stabilizing the ascorbic acid compound in the composition thereby increasing the shelf life of the composition.

The compounds present in the disinfectant composition may also be in kit form, in which a first component is provided that comprises the ascorbic acid compound, preferably containing monothioglycerol, and preferably formulated and packaged in an environment that is substantially devoid of free oxygen, and a second component that contains the other compounds present in the composition. At the time of intended use, the two components are mixed together to produce an ambient temperature soft contact lens disinfecting solution.

DETAILED DESCRIPTION OF THE INVENTION

The aqueous ambient temperature disinfecting compositions for soft and semi-hard contact lenses of the present invention contain a disinfectant ascorbic acid compound. Thus, the compositions in accordance with the invention act as a disinfectant for contact lenses without the necessity for heating. The compositions are particularly useful for disinfecting soft or semi-hard lenses. Suitable disinfectant ascorbic acid compounds include ascorbic acid, sodium ascorbate, calcium ascorbate and mixtures thereof. It is anticipated that other salts of ascorbic acid may also be effectively utilized as a disinfectant. As used herein, the term "disinfectant" means a substance that destroys or kills bacteria, fungi, yeasts or viruses. "Ascorbic acid" is equivalent to "L-ascorbic acid" or "L-xyloascorbic acid." Preferably, the ascorbic acid compound is present in the composition of the present invention as a sodium salt or ascorbic acid, sodium ascorbate.

The ascorbic acid compound is present in the composition of the present invention in a concentration sufficient to provide a disinfectant solution for soft contact lenses. Generally, an amount of between about 0.1% and 20% by weight of the total composition calculated as ascorbic acid is a sufficient concentration to provide a disinfectant solution for soft contact lenses. Thus, the actual weight percent of the ascorbic acid salt will be that weight percent of salt required to achieve a molar concentration of the ascorbic acid ion that is equal to the molar concentration of ascorbic acid at a given weight percent. For example, if it is desired to produce a solution of an ascorbic acid salt equivalent to 10% by weight ascorbic acid, the molar concentration "x", of a 10% by weight solution of ascorbic acid is computed. The weight percent of the ascorbic acid salt required to provide an ascorbic acid ion molar concentration of that amount, "x" is the actual weight of the ascorbic acid salt that is utilized. Preferably, ascorbic acid compound is present in an amount of about 10% by weight of the total composition, calculated as ascorbic acid. It is known that L-ascorbic acid is readily oxidized. Therefore, in accordance with the preferred embodiment of the invention the sodium salt of ascorbic acid is utilized, sodium ascorbate.

In D value studies to demonstrate the log kill of microorganisms, ascorbic acid at concentrations of 1.0% to 5.0% was shown to produce a significant log kill of 5 selected microorganisms, including *Psuedomonas aeruginosa* and *Sephylococcus aureus* within a six hour time period. Since ascorbic acid is naturally present in the human body and is nontoxic to ocular tissue in relatively large amounts, it is believed to be a safe and efficacious ingredient.

In a preferred embodiment of the invention, monothioglycerol is included in an amount effective to stabilize the ascorbic acid compound. Most preferably, in this embodiment, monothioglycerol, is present in a weight ratio of monothioglycerol to the ascorbic acid compound, calculated on the basis of ascorbic acid, of 1:50. Thus, for example, if the concentration of the ascorbic acid compound is 10%, calculated on the basis of ascorbic acid, the concentration of monothioglycerol is 0.2% by weight.

In order to enhance the disinfectant properties of the composition in accordance with the present invention, a potentiating agent compound, selected from the group consisting of trimethoprim, thimerosal and mixtures thereof, is preferably included in an effective amount for providing a disinfectant composition in combination with an ascorbic acid compound for enhancing the D value kill factor relating to bacteria, fungus, yeast and viral organisms. Generally, an effective amount of the potentiating agent is between about 0.0001% and 5.0% by weight of the total composition. Preferably, the potentiating agent is present in an amount of about 0.005% by weight of the total composition.

In order to further increase the shelf life, the compositions are formulated and packaged in an atmosphere that is substantially devoid of free oxygen. For example, the compositions can be formulated and sealed in sterile containers, in the presence of a nitrogen or carbon dioxide atmosphere. Further, it is advantageous for the ascorbic acid compound to be packaged in a non-transparent container to reduce degradation that can be caused by ultraviolet radiation.

The compositions of the present invention preferably include at least one essentially neutral water-soluble compatible salt to provide tonicity equivalent to between about 0.8% and 1.8% sodium chloride by weight of the total aqueous composition. Thus, the preferred compositions according to the invention provide a tonicity which is about the same as or slightly higher than the tonicity of normal human tear fluid. While hypertonic solutions can be desirable since the solution will have a greater osmotic pressure than that of the tear fluid of the contact lens wearer, any soluble salts or mixtures of salts, compatible with ocular tissue, can be used to provide the desired tonicity. Preferably, sodium chloride, potassium chloride or mixtures thereof, are used to provide the desired tonicity. It is understood, however, that one or more essentially neutral, water-soluble alkali or alkaline earth metal salts can be substituted in whole or in part for the sodium or potassium chloride in the solutions of the invention, when tonicity adjustment is desired. Preferably, sodium chloride and potassium chloride are utilized in a weight ratio of between about 2:1 and 7:3, respectively.

A salt of ethylenediaminetetraacetic acid may be included as a buffering agent for the ambient temperature disinfectant solution of the invention for maintaining the pH of the composition in an acid range, preferably between about 4.0 and 7.0. Further, salts of ethylenediaminetetraacetic acid have also been demonstrated to have antibacterial and antifungal properties. The preferred salt of ethylenediaminetetraacetic acid is disodium ethylenediaminetetraacetate, and is preferably present in a concentration of from about 0.05% to about 2.0% by weight of the total aqueous composition and most preferably present in an amount of about 0.1% by weight of the total aqueous composition.

Propylene glycol may optionally be included in the compositions, generally in an amount between about 0.2% and about 2.5% by weight of the total aqueous composition and preferably in an amount of about 0.70% by weight of the total aqueous composition. The propylene glycol acts as a humectant, preservative and fungal growth inhibitor.

In accordance with another preferred embodiment of the present invention, the ascorbic acid compound is utilized together with monothioglycerol, the two compounds being separated from the other components present in the total composition until the time of intended use. Water may or may not be included in the combination of the ascorbic acid compound and monothioglycerol. Thus, the ambient teperature disinfecting composition can be packaged in kit form in which a first component, containing a mixture of the ascorbic acid compound, in solid form, partially or completely dissolved in water, and monothioglycerol. The first component can be formulated and packaged in a sealed sterile container, preferably packaged in an environment substantially free of free oxygen, such as a carbon dioxide or nitrogen atmosphere, to maximize shelf life. A second component containing water and other compounds that may be present in the composition are contained in a second container. When one desires to use the disinfectant solution, the two components are mixed together before utilization.

In accordance with one embodiment of the present invention, a treatment method is provided for killing bacteria associated with contact lenses. A contact lens is treated by storing the lens in an aqueous solution containing a disinfectant ascorbic acid compound present in an effective concentration for killing bacteria. Any of the solutions in accordance with the invention can be used. The lens is brought into contact with an aqueous composition in accordance with the invention for a period of time sufficient for the composition to kill at least a portion of the bacteria associated with the contact lens. For example, the lens is introduced into a container having a solution in accordance with the invention in an amount sufficient to completely immerse the lens. The container is then closed and the contact lens is allowed to remain in the solution for a time sufficient to disinfect the contact lens. No external source of heat is applied and thus, the lens is stored at ambient temperature. Generally, storing the lens in a solution in accordance with the invention for about six hours will provide sufficient disinfection of the contact lens or bacteria for wearing the lens. Thus, the method is ideal for overnight storage of contact lenses or storage between wearing periods. However, it is anticipated that for some solutions in accordance with the invention, less than six hours of storage will be sufficient.

In accordance with the method of the invention, heating of the solution or lens is not required. Thus, the solutions and method of the present invention allow the lens to be disinfected at ambient temperature, eliminating possibility of deleterious effects that may occur when the lens is heated.

The aqueous composition in accordance with the invention is preferably utilized as part of the total patient regimen for maintaining and treating soft, silicone and semi-hard lenses. Thus, an effective cleaning step or steps is an important part of any effective soft or semi-hard lens treatment and maintenance regimen. Separate cleaning of the lenses insures that the disinfectant properties of the aqueous solution will not be overwhelmed by gross organic or inorganic deposits and pollutants.

Whereas the present invention has been described with respect to specific embodiments, it will be understood that various changes and modifications will be suggested to one skilled in the art and it is intended that the invention encompass such changes and modifications as fall within the scope of the appended claims.

We claim:

1. A method of treating a contact lens to kill bacteria associated therewith comprising:
   (a) placing the lens in contact with an aqueous composition, said composition consisting essentially of water and a disinfectant ascorbic acid compound present in an effective amount to kill bacteria; and
   (b) maintaining the lens in contact with said aqueous composition for time sufficient to kill bacteria.

2. The method as recited in claim 1 wherein the lens is completely immersed in said aqueous composition for a period of about six hours.

3. The method as recited in claim 1 wherein the lens is completely immersed in said aqueous composition overnight or between wearing periods.

4. The method as recited in claim 1 wherein said ascorbic acid compound is selected from the group consisting of ascorbic acid, sodium ascorbate, calcium ascorbate and mixtures thereof.

5. The method as recited in claim 4 wherein the concentration of said ascorbic acid compound is between about 0.1% and 20% by weight of the total aqueous composition calculated as ascorbic acid.

6. The method as recited in claim 1 wherein said aqueous composition further consists essentially of an additional compound selected from the group consisting of trimethoprim, thimerosal and mixtures thereof present in an effective amount, in combination with said ascorbic acid compound, for disinfecting soft contact lenses from bacterial, fungal and yeast organisms.

7. The method as recited in claim 6 wherein said additional compound is trimethoprim and is present in an amount of between about 0.0001% and 5.0% by weight of the total aqueous composition and said ascorbic acid compound is present in an amount of between about 0.1% and 20% by weight of the total aqueous composition, calculated as ascorbic acid.

8. A method of treating a contact lens comprising completely immersing the lens in a composition comprising water and a disinfectant composition, said disinfectant composition consisting essentially of a compound selected from the group consisting of ascorbic acid, sodium ascorbate, calcium ascorbate and mixtures thereof.

9. A method of disinfecting a contact lens comprising:
(a) placing the lens in contact with a composition comprising water and a disinfectant composition, said disinfectant composition consisting essentially of first and second components, said first component selected from the group consisting of ascorbic acid, sodium ascorbate, calcium ascorbate and mixtures thereof, said first component present in an amount of between about 0.1% and 20% by weight of the total solution calculated as ascorbic acid, and said second component selected from the group consisting of trimethoprim, thimerosal and mixtures thereof, said second component present in an amount of between about 0.0001% and 5.0% by weight of the total component; and
(b) maintaining the lens in contact with the solution for a time sufficient for disinfection of the lens.

10. A method for treating a contact lens comprising: mixing first and second components together to form a disinfecting composition, said first component consisting essentially of an ascorbic acid compound having disinfectant properties and present in an amount such that when mixed with said second component, said ascorbic acid compound is present in an amount of between about 0.1% and 20% by weight of the total composition, calculated as ascorbic acid, said first component optionally containing an effective amount of monothioglycerol for stabilizing said ascorbic acid compound, said second component consisting essentially of a potentiating agent for said ascorbic acid compound selected from the group consisting of trimethoprim, thimerosal and mixtures thereof, said poteniating agent present in an amount sufficient to provide a concentration, when both components are combined, of between about 0.0001% and 5.0% by weight of the total composition.

11. A composition for ambient temperature disinfection of contact lenses consisting essentially of:
(a) an ascorbic acid compound selected from the group consisting of: ascorbic acid; a salt of ascorbic acid having disinfectant properties and compatible with the contact lenses; and mixtures thereof, said ascorbic acid compound present in an amount of between about 0.1% and 20.0% by weight of the total aqueous composition calculated on the basis of ascorbic acid;
(b) potentiating agent selected from the group consisting of trimethoprim, thimerosal and mixtures thereof and present in an amount of between about 0.0001% and 5.0% by weight of the total aqueous composition;
(c) monothioglycerol present in an effective amount for stabilizing said ascorbic acid or salt thereof; and
(d) the composition being formulated in an atmosphere having substantially no free oxygen and packaged in a sealed container containing substantially no free oxygen.

12. The composition as recited in claim 11 wherein said monothioglycerol is present in a ratio of monothioglycerol to said ascorbic acid compound of about 1:50 calculated as ascorbic acid.

13. The composition as recited in claim 12 wherein said ascorbic acid compound is selected from the group consisting of ascorbic acid, sodium ascorbate, calcium ascorbate and mixtures thereof.

14. The composition as recited in claim 11 wherein the atmosphere selected from the group consisting of carbon dioxide, nitrogen and mixtures thereof.

15. The composition as recited in claim 11 wherein said ascorbic acid compound and said monothioglycerol are separated from the other active components present in the composition until the time of intended use.

16. A method for treating a contact lens comprising placing the lens in contact with the composition as recited in claims 11, 12, 13, 14 or 15 and maintaining said contact for a time sufficient to kill bacteria.

* * * * *

UNITED STATES PATENT AND TRADEMARK OFFICE
CERTIFICATE OF CORRECTION

PATENT NO. : 4,401,582

DATED : August 30, 1983

INVENTOR(S) : Guy J. Sherman

It is certified that error appears in the above-identified patent and that said Letters Patent is hereby corrected as shown below:

Column 2, line 64, delete "comrises" and insert --comprises--;

Column 3, line 22, delete "trimethoxygenzyl" and insert --trimethoxybenzyl--;
Column 3, line 22, after "pyrimidine" delete "," and insert --)--;
Column 4, line 26, after "weight" insert --percent--;
Column 4, line 38, delete "Sephylococcus" and insert --Stephylococcus--; and
Column 5, line 57, delete "teperature" and insert --temperature--.

Signed and Sealed this

*Twenty-first* Day of *August 1984*

[SEAL]

*Attest:*

GERALD J. MOSSINGHOFF

*Attesting Officer*     *Commissioner of Patents and Trademarks*